(12) United States Patent
Tadokoro et al.

(10) Patent No.: US 7,413,548 B2
(45) Date of Patent: Aug. 19, 2008

(54) AUTONOMIC NERVOUS ACTIVITY MONITOR, BLOOD PROCESSING APPARATUS, BLOOD COLLECTING APPARATUS AND AUTONOMIC NERVOUS ACTIVITY MONITORING METHOD

(75) Inventors: Kenji Tadokoro, Nagareyama (JP); Fumiko Saitou, Sagamihara (JP); Yoshiki Takagi, Fuji (JP)

(73) Assignees: Japanese Red Cross Society, Minato-Ku, Tokyo (JP); Terumo Kabushiki Kaisha, Shibuya-Ku, Tokyo (JP)

( * ) Notice: Subject to any disclaimer, the term of this patent is extended or adjusted under 35 U.S.C. 154(b) by 417 days.

(21) Appl. No.: 11/083,213

(22) Filed: Mar. 18, 2005

(65) Prior Publication Data

US 2005/0209522 A1    Sep. 22, 2005

(30) Foreign Application Priority Data

Mar. 19, 2004    (JP)    ............................. 2004-081617

(51) Int. Cl.
*A61B 5/02*    (2006.01)
(52) U.S. Cl. .................... 600/500; 604/4.01; 604/66
(58) Field of Classification Search ................ 600/508, 600/500; 604/4.01, 6.01, 7, 8, 66
See application file for complete search history.

(56) References Cited

U.S. PATENT DOCUMENTS 5,682,901 A * 11/1997 Kamen ........................ 600/519
2002/0120306 A1 * 8/2002 Zhu et al. ..................... 607/25
2003/0078505 A1 * 4/2003 Kim et al. .................... 600/485
2003/0097075 A1 * 5/2003 Kuo ............................. 600/500
2003/0135126 A1 * 7/2003 Kuo ............................. 600/513
2004/0054292 A1 * 3/2004 Sun et al. .................... 600/504

FOREIGN PATENT DOCUMENTS

JP    5-054994    8/1993
JP    2000-287945    10/2000

OTHER PUBLICATIONS

Mika Seto, et al., "Assessment of Autonomic Nervous Activity Using Spectral Analysis of Heart Rate and Blood Pressure Variability in Autologous Blood Donation and Crystalloid or Colloid Infusion", Japanese Journal of Transfusion Medicine, 2002, pp. 455-464, vol. 48, No. 6 (with partial English translation).

* cited by examiner

*Primary Examiner*—Charles A. Marmor, II
*Assistant Examiner*—Anita Saidi
(74) *Attorney, Agent, or Firm*—Buchanan Ingersoll & Rooney PC

(57) ABSTRACT

An autonomic nervous activity monitor capable of predicting occurrence of abnormal reaction depending on autonomic nervous activity and used for medical practice and the like is provided. A blood component collecting apparatus 100 carries out frequency analysis to a pattern of heartbeat which is acquired by an ECG 300 from a donor, and calculates a high frequency component value [$msec^2$] defined as an indicator for parasympathetic activity and a ratio value of a low frequency component to the high frequency component defined as an indicator for sympathetic activity to detect a change in these values on a time-series base. When a judgment circuit 204 predicts that abnormal reaction may occur to a donor after blood collection operation is started, a controller 200 controls a pump 9 to decrease a blood drawing or blood returning speed, or, to stop blood drawing or blood returning operation.

6 Claims, 3 Drawing Sheets

AUTONOMIC NERVOUS ACTIVITY MONITOR, BLOOD PROCESSING APPARATUS, BLOOD COLLECTING APPARATUS AND AUTONOMIC NERVOUS ACTIVITY MONITORING METHOD

BACKGROUND OF THE INVENTION

1. Field of the Invention

The present invention relates to an autonomic nervous activity monitor, a blood processing apparatus, a blood collecting apparatus and an autonomic nervous activity monitoring method.

2. Description of the Related Art

Vasovagal reactions (VVR), delayed dizziness or faintness often occur(s) to a donor or patient during or after blood collection as adverse reaction (abnormal reaction).

The VVR may cause the donor or patient bad feeling, dizziness, faintness or shock disease during blood collection, and the donor or patient occasionally falls into serious conditions. Because such phenomena harm the donor or patient mentally due to implantation of a fear to blood collection, it is likely to have a trouble thereafter in blood collection, medical treatment or the like. Further, such a case is reported that a donor or patient was taken to the hospital since he/she fell to strike his/her head due to dizziness or faintness after he/she left a blood collection room.

In order to solve these problems, it seems effective if there is an apparatus with which a donor or patient can carry during a period of before blood collection to after blood collection and which can measure blood pressure to inform an operator an abnormal situation of the donor or patient immediately. However, such an apparatus does not exist, and it is all to measure blood pressure or pulse before and after blood collection at a consultation room or a bed in the present situation, as disclosed, for example, in JPA 2000-287945. In a case that blood pressure is measured before blood collection, a circulatory situation at that time can be grasped to some degree. But, it is difficult to predict and prevent adverse reaction which occurs to a donor or patient after his/her leaving a blood collection room.

SUMMARY OF THE INVENTION

In view of the above circumstances, an object of the present invention is to provide an autonomic nervous activity monitor which can predict occurrence of abnormal reaction (adverse reaction) according to autonomic nervous activity, a blood processing apparatus or a blood collecting apparatus which equips the autonomic nervous activity monitor, and an autonomic nervous activity monitoring method thereof, for example, for medical treatment or the like.

In order to achieve the above object, a first aspect of the present invention is directed to an autonomic nervous activity monitor that monitors autonomic nervous activity of a body, comprising: a biological information acquisition unit which measures heartbeat or pulse of a body to acquire a pattern of the heartbeat or pulse as biological information; a calculation unit which calculates a value [$msec^2$] of a high frequency component (a HF value) defined as an indicator for parasympathetic activity and a value of a ratio of a low frequency component (LF) to the high frequency component (a LF/HF ratio value) defined as an indicator for sympathetic activity on a time-series base by carrying out frequency analysis to the pattern of the heartbeat or pulse acquired by the biological information acquisition unit; a prediction unit which predicts whether abnormal reaction may occur to the body from a predetermined relationship between the HF value and the LF/HF ratio value, based upon the HF values and the LF/HF ratio values calculated by the calculation unit; and an information unit which, when the prediction unit predicts that abnormal reaction may occur to the body, informs an operator that abnormal reaction may occur.

In the first aspect, it is preferable that, when alpha is defined as a predetermined coefficient and beta is defined as a predetermined coefficient which is larger than the coefficient alpha, the prediction unit predicts that abnormal reaction may occur to the body when the HF value calculated by the calculation unit exceeds a predetermined reference value and when a sum of a period of {(the HF value calculated by the calculation unit)>(the coefficient alpha)×(the LF/HF ratio value calculated by the calculation unit)} becomes not less than 10% of a calculation period carried out by the calculation unit, or, when a sum of a period of {(the HF value calculated by the calculation unit)>(the coefficient beta)×(the LF/HF ratio value calculated by the calculation unit)} becomes not less than 10% of the calculation period carried out by the calculation unit, and it is more preferable that the predetermined reference value ranges from 100 to 1000 [$msec^2$], the coefficient alpha ranges from 10 to 100, the coefficient beta ranges from 25 to 500 and the calculation period ranges from 2 to 10 [min].

Further, in order to achieve the above object, a second aspect of the present invention is directed to a blood processing apparatus that carries out blood drawing operation for drawing blood from a body and blood returning operation for returning blood to the body, comprising: a biological information acquisition unit which measures heartbeat or pulse of a body to acquire a pattern of the heartbeat or pulse as biological information; a calculation unit which calculates a value [$msec^2$] of a high frequency component (a HF value) defined as an indicator for parasympathetic activity and a value of a ratio of a low frequency component (LF) to the high frequency component (a LF/HF ratio value) defined as an indicator for sympathetic activity on a time-series base by carrying out frequency analysis to the pattern of the heartbeat or pulse acquired by the biological information acquisition unit; a blood drawing unit which carries out the blood drawing operation to the body; a blood processing unit which processes blood drawn from the body by the blood drawing unit; a blood returning unit which returns to the body blood processed by the blood processing unit; and a controlling unit which controls the blood drawing unit, the blood processing unit and the blood returning unit, and which predicts whether abnormal reaction may occur to the body from a predetermined relationship between the HF value and the LF/HF ratio value, based upon the HF values and the LF/HF ratio values calculated by the calculation unit, wherein the controlling unit, when predicted that abnormal reaction may occur to the body after starting the blood drawing operation of the blood drawing unit, reduces a rate for drawing blood from the body according to the blood drawing unit or a rate for returning blood to the body according to the blood returning unit, or, stops the blood drawing operation of the blood drawing unit or the blood returning operation of the blood returning unit.

Furthermore, in order to achieve the above object, a third aspect of the present invention is directed to a blood collecting apparatus that carries out blood collection operation to a body, comprising: a biological information acquisition unit which measures heartbeat or pulse of a body to acquire a pattern of the heartbeat or pulse as biological information; a calculation unit which calculates a value [$msec^2$] of a high frequency component (a HF value) defined as an indicator for parasympathetic activity and a value of a ratio of a low frequency component (LF) to the high frequency component (a LF/HF ratio value) defined as an indicator for sympathetic activity on a time-series base by carrying out frequency analysis to the pattern of the heartbeat or pulse acquired by the biological information acquisition unit; a blood collection unit which carries out the blood collection operation to the body; and a controlling unit which controls the blood collection unit and which predicts whether abnormal reaction may occur to the body from a predetermined relationship between the HF value and the LF/HF ratio value, based upon the HF values and the LF/HF ratio values calculated by the calculation unit, wherein the controlling unit, when predicted that abnormal reaction may occur to the body after starting the blood collection operation of the blood processing unit, reduces a rate for collecting blood from the body according to the blood collection unit, or, stops the collection operation of the blood collection unit.

In the above second and third aspects, it is preferable that, when alpha is defined as a predetermined coefficient, the controlling unit predicts that abnormal reaction may occur to the body when a sum of a period of {(the HF value calculated by the calculation unit)>(the coefficient alpha)×(the LF/HF ratio value calculated by the calculation unit)} becomes not less than 75% of a calculation period carried out by the calculation unit, and it is more preferable that the coefficient alpha ranges from 10 to 100 and the calculation period ranges from 1.25 to 10 [min]. Further, the apparatus may further comprising an information unit which, when the controlling unit predicts that abnormal reaction may occur to the body, informs an operator that abnormal reaction may occur.

And, the fourth aspect of the present invention is directed to an autonomic nervous activity monitoring method for predicting whether abnormal reaction may occur to a body, comprising the steps of: measuring heartbeat or pulse of a body to acquire a pattern of the heartbeat or pulse as biological information; calculating a value [msec$^2$] of a high frequency component (a HF value) defined as an indicator for parasympathetic activity and a value of a ratio of a low frequency component (LF) to the high frequency component (a LF/HF ratio value) defined as an indicator for sympathetic activity on a time-series base by carrying out frequency analysis to the acquired pattern of the heartbeat or pulse; and predicting whether abnormal reaction may occur to the body from a predetermined relationship between the HF value and the LF/HF ratio value, based upon the calculated HF values and the calculated LF/HF ratio values.

According to the present invention, for example, for medical treatment, daily activity or the like, occurrence of pressure drop, dizziness or faintness according to autonomic nervous activity such as vasovagal reaction (VVR) can be predicted to prevent occurrence of such condition in advance.

DETAILED DESCRIPTION OF THE PREFERRED EMBODIMENTS

An embodiment of a blood component collecting apparatus to which the present invention is applicable will be explained in detail below.

Figure 1:
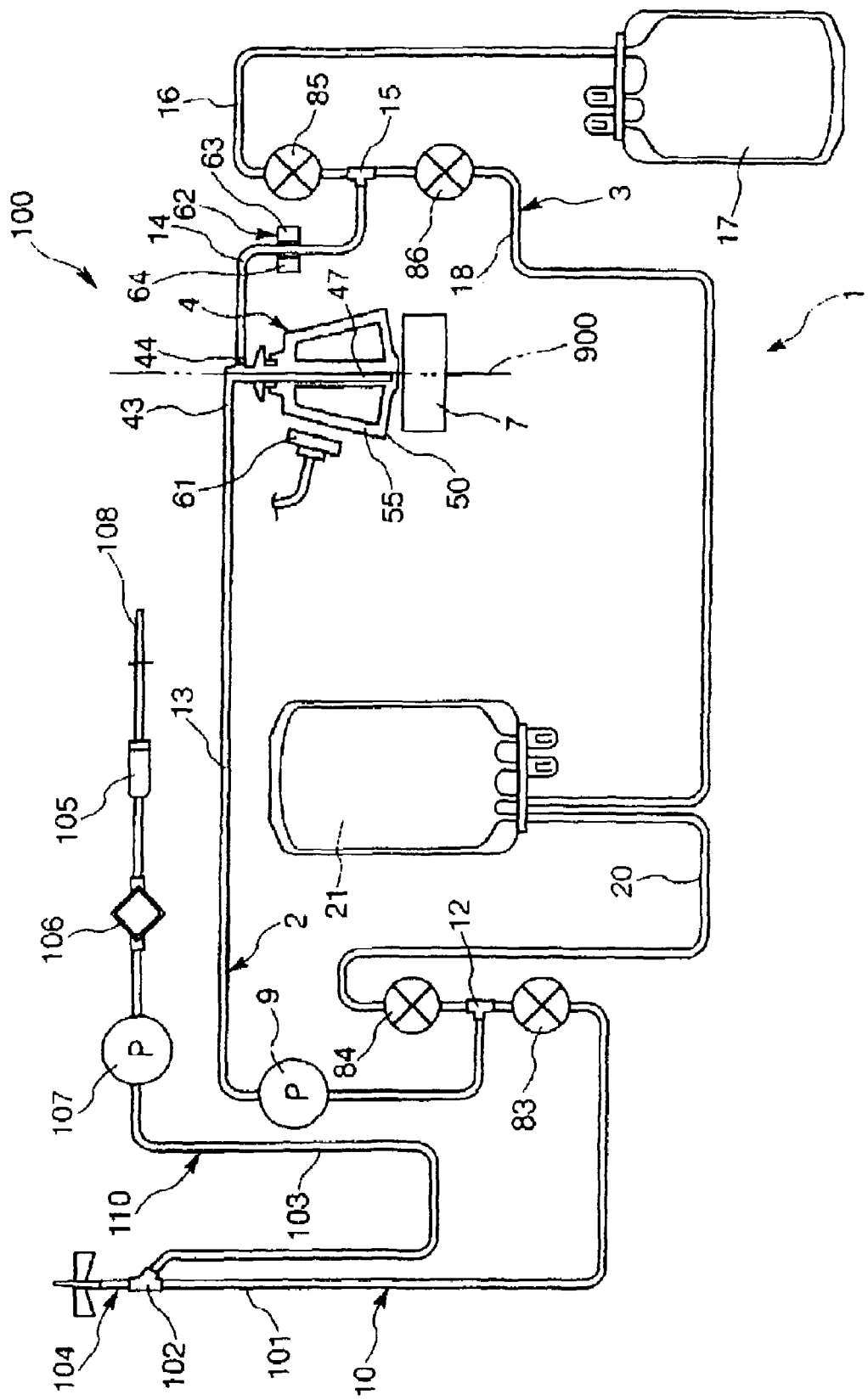
FIG. 1 is a system diagram of a blood component collecting apparatus in an embodiment to which the present invention is applicable.

As shown in FIG. 1, a blood component collecting apparatus (blood processing apparatus) 100 of this embodiment is an apparatus which carries out a series of operation such as collecting (drawing) blood from a donor who is a normal subject, separating the collected blood into a plurality of blood components to collect the separated blood components, and then returning remaining blood components to the donor. The blood component collecting apparatus 100 has a blood component collection circuit (blood processing circuit) 1 which serves as a blood drawing unit (a blood collection unit), a blood processing unit and a blood returning unit.

The blood component collection circuit 1 is a circuit for collecting blood platelet from blood and is constituted by equipping a centrifugal separator 4 for separating blood into a plurality of blood components, a first line (blood introduction line) 2 for introducing blood to the centrifugal separator 4, a second line (blood component collection line) 3 for collecting the blood components separated by the centrifugal separator 4, a third line (drawing/returning line) 10 for being to be connected with a blood vessel of a donor, and a fourth line 110 for adding anticoagulant to blood.

Figure 2:
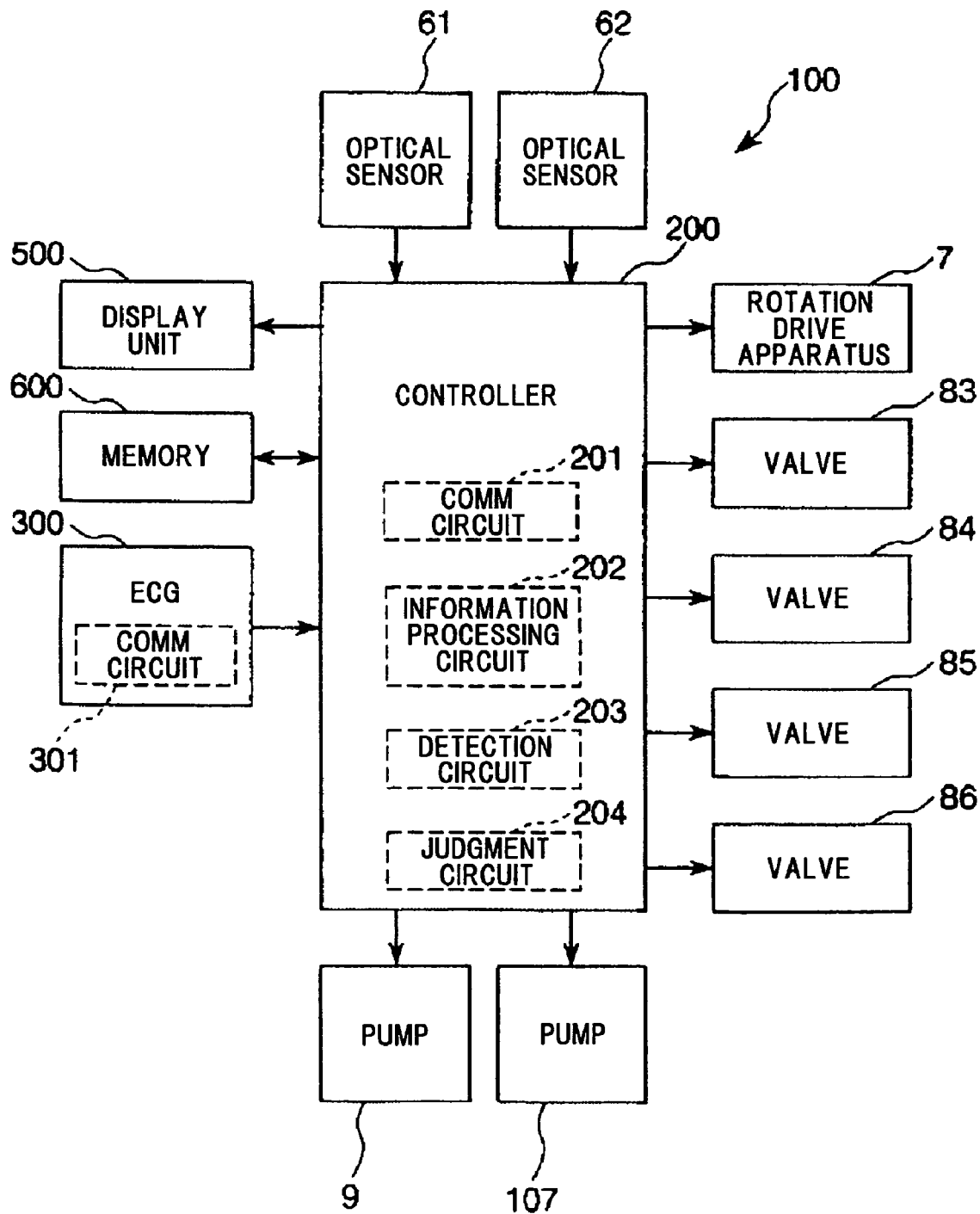
FIG. 2 is a block diagram of the blood component collecting apparatus in the embodiment.

Further, as shown in FIG. 1 and FIG. 2, the blood component collecting apparatus 100 has a rotation drive apparatus 7 which rotates a rotor 50 of the centrifugal separator 4, optical sensors 61, 62, a pump 9 which is disposed at the first line 2, a pump 107 which is disposed at the fourth line 110, an electrocardiograph (ECG) 300 which serves as a biological information acquisition unit, a display unit 500 which serves as an information unit, a memory 600, valves 83, 84, 85 and 86, and a controller 200 which controls operation of each portion of the blood component collecting apparatus 100 such as the optical sensors 61, 62, the pumps 9, 107, the rotation drive apparatus 7 and each of the valves 83 to 86.

Among these portions, an autonomic nervous activity monitor of the present invention is constituted by the ECG 300, the display unit 500, the memory 600 and the controller 200 (an information processing circuit 202, a detection circuit 203, a judgment circuit 204 stated later).

(Structure)

The structure of each portion of the blood component collecting apparatus 100 in this embodiment will be explained one by one below.

As shown in FIG. 1, the third line 10 is mainly structured by a tube 101 and a blood collection needle (puncture needle) 104 which is connected to a tip of the tube 101. A base end of the tube 101 is connected to one ends of tubes 13 and 20 via a T-shaped branch connector 12. A valve 83 which disconnects/connects an internal channel of the tube 101 is disposed midway the tube 101. Further, a tube 103 is connected to the tube 101 via a Y-shaped branch connector 102.

The fourth line 110 is structured by the tube 103, a spike 108 which is connected to a tip of the tube 103, a drip infusion cylinder 105 and an antibacterial filter 106 both connected midway the tube 103. The pump 107 for adding anticoagulant and which is constituted of, for example, a roller pump, is disposed midway the tube 103.

The first line 2 is structured by the tube 13 and the branch connector 12 which is connected to one end of the tube 13. Another end of the tube 13 is connected to an inflow port 43 of the centrifugal separator 4. The pump 9 for sending (drawing and returning) blood and which is constituted of, for example, a roller pump, is disposed midway the tube 103. A rate for drawing and returning blood from/to a donor is adjustable by controlling operation of the pump 9.

One end of the tube 14 is connected to an outflow port 44 of the centrifugal separator 4, and another end of the tube 14 is connected to one ends of tubes 16 and 18 via a T-shaped branch connector 15. Another end of the tube 16 is connected to a blood platelet bag 17 for collecting blood platelet, and the valve 85 which opens/closes a channel (flowing path) of the tube 16 is disposed midway the tube 16. Another end of the tube 18 is connected to a blood plasma bag 21, and the valve 86 which opens/closes a channel of the tube 18 is disposed midway the tube 18. Another end of the tube 20 of which one end is connected to the branch connector 12 is connected to the blood plasma bag 21, and the valve 84 which opens/closes a channel of the tube 20 is disposed midway the tube 20.

In such a structure, the second line 13 is constituted by the tubes 14, 16, 18, 20, the branch connector 15, the blood platelet bag 17 and the blood plasma bag 21. Among these, the tubes 14, 18 and the blood plasma bag 21 constitute a branched line for collecting blood plasma, and the tubes 14, 16 and the blood platelet bag 17 constitute a branched line for collecting blood platelet.

The rotation drive apparatus 7 is structured, for example, by a housing which accommodates the centrifugal separator 4, a disc-shaped anchor block which supports the rotor 50 of the centrifugal separator 4 and a motor which drives to rotate the anchor block, each being unillustrated.

The optical sensor 61, which optically detects an interface of separated blood components, namely, a position of an interface between a blood plasma layer and a blood cell layer in the rotor 50, is disposed so as to face an outer peripheral surface of the rotor 50. This optical sensor 61 has a light emitting element such as an LED and a light receiving (detecting) element such as a photodiode, and is constituted such that the light detecting element receives reflected light of the light which is emitted from the light emitting element and converts quantity of the received light photo-electrically. Since intensity of reflected light in the blood plasma layer is different from that in the blood cell layer, a position, at which quantity of receiving light, namely, output voltage changes, is detected as the position of the interface by the light receiving element.

An optical sensor 62, capable of detecting density or concentration of the blood platelet in the blood components which flows in the tube 14, is disposed between the outflow port 44 of the tube 14 and the branch connector 15. This optical sensor 62 is constituted by a light emitting portion (light source) 63 and a light receiving portion (photodiode) 64, each being disposed to face each other via the tube 14. The light (ex. laser beam) emitted from the light emitting portion 63 and which transmitted the tube 14 is received to convert into an electric signal according to quantity of the received light by the light receiving portion 64. Because transmissivity changes in accordance with density (concentration) of blood platelet in blood components which flows inside the tube 14 and the quantity of the light received by the light receiving portion 64 fluctuates, fluctuation thereof can be detected as a change in output voltage from the light receiving portion 64.

Each of the valves 83 to 86 is driven by a driving source, for example, such as a solenoid, a electric motor, a cylinder (oil pressure or air pressure) or the like. Such a driving source is operated based upon (a) signal(s) from the controller 200.

The ECG 300 acquires reaction of a donor (body) derived from his/her autonomic nervous activity as biological information. It is preferable that the ECG 300 is used in a state that a donor is wearing his/her clothes such as a wristband type, a manchette type, a finger type or the like. In other words, it is preferable that the ECG 300 obtains biological information noninvasively or bloodlessly. This makes application easy to such a blood component collecting apparatus 100, like this embodiment, which is used for a donor who provides blood.

Further, as shown in FIG. 2, the ECG 300 has a communication circuit 301. The communication circuit 301 is capable of wireless communication with a communication circuit 201 which the controller 200 has and which will be explained later. Thus, the ECG 300 can transmit the acquired biological information to the memory 600 by wireless communication.

Such a structure lightens a donor in feeling as if he/she were bound by the blood component collecting apparatus 100 (feeling of pressure), as a result of this, which can decrease uneasiness/strain which is one of factors causing, for example, VVR, delayed dizziness, faintness or the like.

The ECG 300 acquires (detects) heartbeat of a donor as biological information, more concretely, detects on a time-series base electrocardiogram which expresses action potential of heart muscle by using three electrodes of a plus electrode, a minus electrode and an E electrode (for grounding) in order to memorize intervals of heartbeat. It is preferable to use a small sized one for this ECG 300. Using such a small sized ECG 300 lightens a donor feeling of pressure.

Incidentally, the ECG 300 may be connected to the controller 200 with wires to transmit the acquired biological information to the memory 600 through the wires (wired communication). Each of the electrodes equipped by the ECG 300 may be either of disposable one or reusable one. In a case that each of the electrodes is disposable, it becomes easy to set/remove the electrodes to/from a donor. Besides, it gives a donor an impression that collection of blood components is carried out hygienically. These also can decrease uneasiness which is one of factors causing adverse reaction. While, in a case that each of the electrodes is reusable, costs for collection of blood components can be reduced.

The controller 200 is constituted, for example, by a microcomputer and the like, and houses the communication circuit 200 which enables wireless communication, an information processing circuit 202 which has a function of calculating a value [$msec^2$] of a high frequency component (a HF value) defined as an indicator for parasympathetic activity and a value of a ratio of a low frequency component (LF) to the high frequency component (a LF/HF ratio value) defined as an indicator for sympathetic activity repeatedly on a time-series base by carrying out frequency analysis to the acquired pattern of the heartbeat (fluctuation of R-R interval detected from electrocardiogram by pattern recognition or the like) and which serves as a part of a calculation unit, a detection circuit 203 which has a function of detecting a time-series based change in the HF values and the LF/HF ratio values and which serves as a part of a calculation unit, and a judgment circuit 204 which has a function of judging as to whether or not abnormal reaction may occur to a donor based upon the results detected by the detection circuit 203 and which serves as a part of a prediction unit or a controlling unit.

The communication circuit 201 receives with wireless communication the heartbeat (biological information) measured and acquired by the ECG 300 and outputs it to the memory 600. The memory 600 memorizes (records) the heartbeat at any time. The information processing circuit 202 reads out the heartbeat memorized in the memory 600 to calculate the HF values and the LF/HF ratio values based upon the heartbeat. Concretely, the information processing circuit 202 carries out frequency analysis to R-R interval of electrocardiogram (pattern of heartbeat) at a predetermined processing interval (ex. about 60 sec) to calculate the HF value and the LF/HF ratio value.

Incidentally, in the frequency analysis, adjacent processing intervals may be set so as not to overlap each other (intermittent output method). However, it is preferable that a part of adjacent processing intervals is set so as to overlap each other (consecutive output method). Further, a fast Fourier transformmethod (FFT method), a maximum entropy method (MEM method), a wavelet transform method or the like can be used for the frequency analysis (time-frequency analysis).

The detection circuit 203 detects a time-series based change in the HF values and the LF/HF ratio values. The judgment circuit 204 predicts, based upon the detection results of the detection circuit 203, that a donor may have the above stated condition of a disease (adverse reaction) during his/her blood collection or after standing up from a blood collection bed afterwards his/her blood collection, when the following Condition A and Condition B are satisfied:

<Condition A>

[Condition A-1]: The HF value exceeds a predetermined reference value, and, a sum of a period of (the HF value)>(a coefficient alpha)×(the LF/HF ratio value) became not less than 10% of a measuring period, or,

[Condition A-2]: A sum of a period of (the HF value)>(a coefficient beta)×(the LF/HF ratio value) became not less than 10% of a measuring period. (coefficient alpha<coefficient beta)

Figure 3:
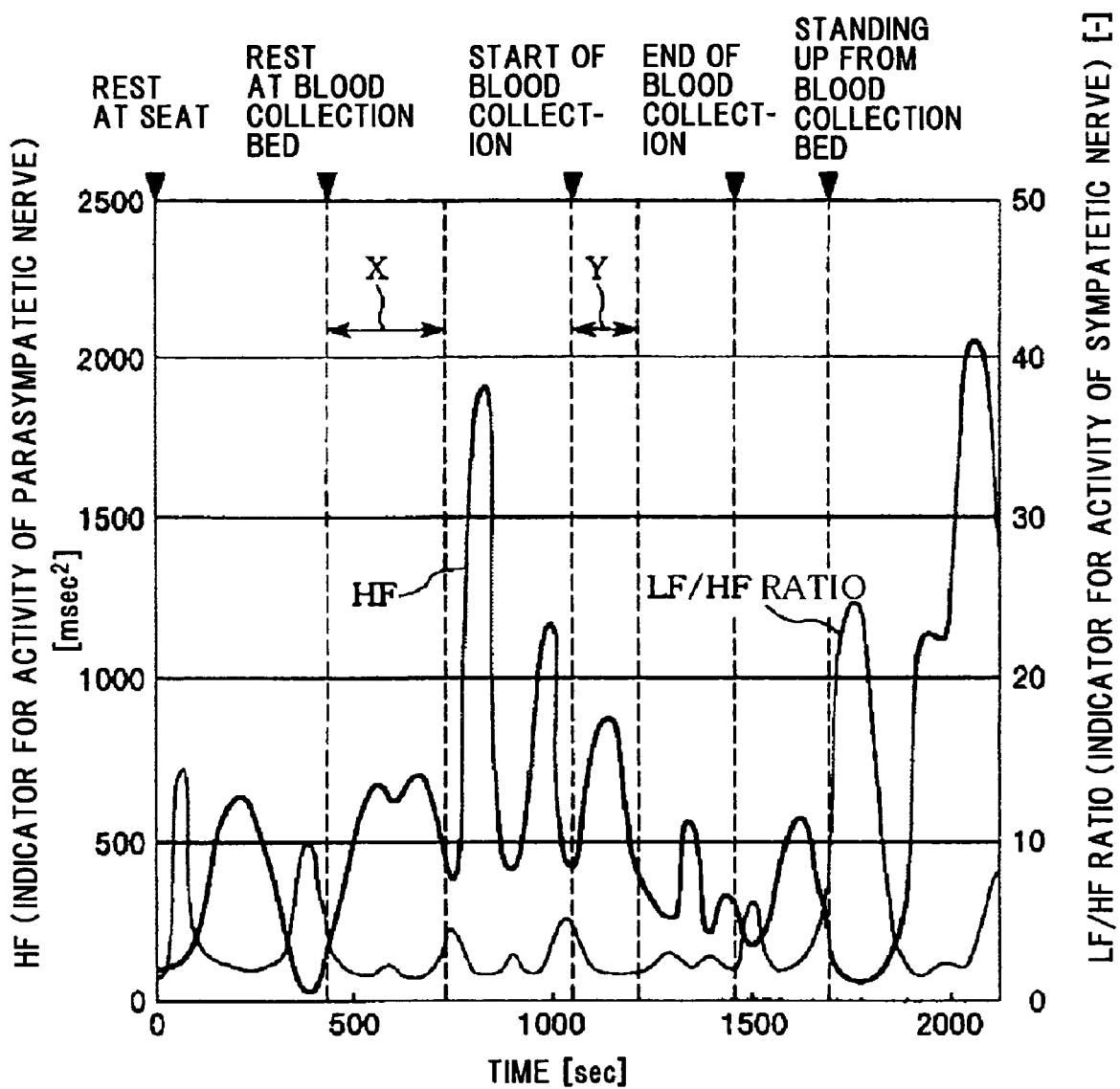
FIG. 3 is a graph showing an example of a time-lapse change in a HF value (an indicator for parasympathetic activity) and a LF/HF ratio value (an indicator for sympathetic activity) according to blood component collection operation.

Here, in a case that the MEMmethod is used for frequency analysis, under Condition A and Condition B, a measuring period, namely, a detection period carried by the detection circuit 203 (a calculation period of a calculation unit) is preferably set to be 2 to 10 min from a moment when a donor takes a rest position at a blood collection bed (a moment of a semisupine position), and more preferably set to be 2.5 to 7.5 min, and, for example, it is set to 5 min, as shown by Period X in FIG. 3.

Under Condition A-1, the reference value of the HF value is preferably set to be 100 to 1000 msec$^2$, and more preferably set to be 200 to 600 msec$^2$, and, for example, set to 400 msec$^2$. The coefficient alpha is preferably set to 10 to 100a, and more preferably set to 25 to 75, and, for example, set to 50. Under Condition A-2, the coefficient beta is set to be larger than the coefficient alpha, it is preferably set to be 25 to 500, more preferably set to 100 to 300, and, for example, set to 200.

<Condition B>

A sum of a period of (the HF value)>(a coefficient alpha)× (the LF/HF ratio value) became not less than 75% of a measuring period.

Here, in a case that the MEMmethod is used for frequency analysis, under Condition B, a measuring period (detection period carried by the detection circuit 203) is preferably set to be 1.25 to 10 min from a moment when blood drawing operation is started, and more preferably set to be 1.5 to 5 min, and, for example, it is set to 2 min, as shown by Period Y in FIG. 3. Further, under Condition B, the coefficient alpha is preferably set to be 10 to 100, more preferably set to 25 to 75, and, for example, it is set to 50.

In a body, sympathetic nerve and parasympathetic nerve, both constituting an autonomic nervous system, commonly function each other competitively. In general, when sympathetic nerve is excited, it functions so as blood pressure to go up or so as heart rate to increase, while, when parasympathetic nerve is excited, it functions so as blood pressure to go down or so as heart rate to decrease. For example, when a body stands up, in order to avoid lowering of blood pressure at an upper part of a body because blood in the body concentrates on a side of legs due to gravitation, sympathetic nerve gets excited to restrain lowering of blood pressure by constricting blood vessels. However, when the balance of the autonomic nervous system becomes upset for some factor, a body can not restrain a change in blood pressure according to the above-stated mechanism and causes a sudden pressure drop after the body stands up. As a result of this, abnormal reaction, for example, such as faintness, VVR according to blood collection or the like occurs.

Inventors made an elaborate study on the abnormal reaction in view of the above circumstances, and found that there was a strong likelihood that a donor causes adverse reaction when the HF value defined as an indicator for expressing an excitement degree of parasympathetic nerve (an indicator for parasympathetic activity) and the LF/HF ratio value defined as an indicator for expressing an excitement degree of sympathetic nerve (an indicator for sympathetic activity) satisfy the above-stated predetermined relationship during the above-mentioned predetermined period. The present invention was made based upon this found matter.

As mentioned above, under Condition A-1 and Condition A-2, the sum of the period that the HF value and the LF/HF ratio value satisfy the above-stated predetermined relationship should be not less than 10% of the measuring period (detection period carried by the detection circuit 203) for the criteria that the judgment circuit 204 judges that a donor may cause adverse reaction after his/her standing up. However, it should be preferably not less than 15%, more preferably not less than 20%. Concretely, when the measuring period is 5 min, it should be not less than 30 sec, preferably not less than 45 sec, more preferably not less than 60 sec.

On the other hand, under Condition B, the sum of the period that the HF value and the LF/HF ratio value satisfy the above-stated predetermined relationship should be not less than 75% of the measuring period (detection period carried by the detection circuit 203). However, it should be preferably not less than 85%, more preferably not less than 95%. Concretely, when the measuring period is 2 min, it should be not less than 90 sec, preferably not less than 102 sec, more preferably not less than 114 sec.

By setting the criterion to such a range, judgment (prediction) having higher accuracy is made by the judgment circuit 204.

It should be noted that the judgment circuit 204 may be constituted such that the criterion can be changed within the above range by an operator of the blood component collecting apparatus 100, based upon the results of asking a donor detailed questions about his/her sex, age, tendency of dizziness or dizziness at standing up (faintness) in daily life and the like. Further, ether one of the Period X and Period Y may be employed for the detection period carried out by the detection circuit 203, however, in a case that both are employed, occurrence of abnormal reaction of a donor can be detected more reliably.

Further, a percentage (%) to amplitude or total power (HF value+LF value) may be substituted for the unit expressing a magnitude of the HF and LF values. Furthermore, since the values, when frequency analysis is made by the FFT method, wavelet transform method or the like, are somewhat different from those when frequency analysis is made by the MEM method, the reference value, coefficients, measuring period for the Condition A and Condition B may be changed appropriately so as to match the frequency analysis.

The controller 200 makes the display unit display (informs) the judgment result made by the judgment circuit 204. Further, when the judgment that a donor may cause adverse reaction is made by the judgment circuit 204 and operation of blood collection has been started, the controller 200 controls operation of the pump 9 so that a rotating speed of the pump 9 is lowered or so that operation of the pump 9 is stopped. Accordingly, adverse reaction that a donor may cause can be prevented from occurring in advance or aggravation thereof can be prevented.

The display unit 500 is structured, for example, by light emitting elements such as light emitting diodes (LED), EL elements or the like, lamps, EL display or liquid crystal display (LCD) and the like, and displays the judgment result made by the judgment circuit 204, for example, with at lease one of numerals such as concrete values or the like of the time that the above Condition A and/or Condition B are/is satisfied, letters of "Danger", "Safe", colors or icons (figures) expressing such contents. Accordingly, an operator (a doctor or a nurse) of the blood component collecting apparatus 100 can grasp a state of a donor easily.

Further, the display unit 500 may always display a change in the HF values and the LF/HF ratio values, a state of autonomic nervous activity and the like. For example, the display unit 500 may display letters of "Sympathetic Nerve Predominant" or "Parasympathetic Nerve Predominant", icons expressing such contents to show the state of autonomic nervous activity. Accordingly, an advantage that an operator of the blood component collecting apparatus 100 can grasp a state of a donor in real time can be obtained.

Incidentally, an information unit of the present invention is not limited to this. The information unit may be constituted by a speech output unit, for example, such as a buzzer (a unit letting out a fixed sound, melody or the like), a unit letting out words (speech) or the like. The information unit may equip both of the display unit and the speech output unit.

(Operating Procedure)

Next, with reference to FIGS. 1 to 3, operation procedure for the blood component collecting apparatus 100 of this embodiment will be explained in the order of process.

<Process [1]>

The blood component collection circuit 1 is set (mounted) to the blood component collecting apparatus 100. The ECG 300 is set to a donor who seated at a waiting room or the like.

Next, the ECG 300 is started in a state that a donor laid down on a blood collection bed (a donor took a semisupine position.). At this time, when the HF value and the LF/HF ratio value detected by the detection circuit 203 satisfy the above stated relationship (Condition A), the judgment circuit 204 judges (predicts) that the donor may cause adverse reaction during collection of blood or after standing up from the blood collection bed, and the controller 200 makes the display unit 500 to display (inform) the judgment result (prediction result) that adverse reaction may occur.

An operator of the blood component collecting apparatus 100 confirms the judgment results displayed by the display unit 500, and then stops blood component collection operation per se, which is carried out in or after the following Process [2]. This prevents adverse reaction of a donor from occurring in advance and can secure safety of a donor. Besides, this prevents the blood component collection circuit 1 from using and wasting uselessly.

On the other hand, when the judgment circuit 204 judges that the HF value and the LF/HF ratio value do not satisfy the above stated relationship, the blood component collection operation which is carried out in or after the following Process [2] is executed continuously.

<Process [2]>

Next, the spike 108 is connected to a bag in which anticoagulant is contained, and priming is carried out to the fourth line 110 and the blood collection needle 104 with anticoagulant. Then, the blood collection needle 104 is needled to a blood vessel of a donor.

<Process [3]>

Next, the pump 9 is operated (normal rotation) in a state that the valves 83 and 85 are opened and other valves are closed. Blood of a donor is conveyed via the tubes 101 and 13, and is introduced to a blood storage space 55 via an inflow tube 47 after flowing into the inflow port 43 of the centrifugal separator 4. Incidentally, a rotational speed of the pump 9 is set to a degree that a discharging amount of blood (a supplying speed of blood) is, for example, 20 to 100 milliliter/min.

Simultaneously, the pump 7 is operated to add anticoagulant (ex. ACD-A liquid) via the spike 108 and the rotation drive apparatus 7 is operated so that the rotor 50 is rotated preferably at 3000 to 6000 rpm (ex. 4800 rpm). Blood flowed in from a lower end aperture of the inflow tube 47 is collected to the blood storage space 55 according to centrifugal force of rotation of the rotor 50, and is separated at the blood storage space 55 in the order of a blood plasma layer, a buffy coat layer and a red blood cell layer from a side of a rotation central axis 900.

At this time, when the HF value and the LF/HF ratio value detected by the detection circuit 203 satisfy the above stated relationship (Condition B), the judgment circuit 204 judges (predicts) that the donor may cause adverse reaction during collection of blood or after standing up from the blood collection bed, and the controller 200 makes the display unit 500 to display (inform) the judgment result (prediction result) that adverse reaction may occur.

Further, in such a case, the controller 200 controls operation of the pump 9 to decrease the drawing speed (rate) or to stop the operation (cancel or suspend blood collection). This prevents adverse reaction of a donor from occurring in advance and can secure safety of a donor.

Incidentally, when the judgment circuit 204 judges that the HF value and the LF/HF ratio value do not satisfy the above stated relationship, or, when the controller 200 controls operation of the pump 9 to decrease the blood collection speed even in a case that the judgment circuit 204 judges that the HF value and the LF/HF ratio value satisfy the above stated relationship, the following blood component collection operation is executed continuously.

<Process [4]>

In a case that the above Process [3] is carried out continuously and blood which exceeds a capacity of the blood storage space 55 (about 270 milliliter) is introduced to the blood storage space 55, the blood storage space 55 is filled with blood perfectly, and blood plasma overflows out of the outflow port 44 of the centrifugal separator 4.

At this time, a change from air to blood plasma in a fluid flowing in the tube 14 is detected by an ultrasonic sensor (not shown) disposed at the second line 3, and the controller 200 controls the valve 85 to close and the valve 86 to open.

Thus, blood plasma is introduced into and collected by the blood plasma bag 21 via the tubes 14 and 18. Accompanied by this, because an amount of red blood cells is increased in the blood storage space 55, an interface between the blood plasma layer and the red blood cell layer is gradually shifted to a side of the rotation central axis 900. The interface is always monitored by the optical sensor 61.

<Process [5]>

Based upon a detected signal (detection information on a position of the interface) that the interface is reached at a predetermined level from the optical sensor 61, the controller 200 controls the valve 83 to close, the valve 84 to open, the pump 107 to stop and the pump 9 to operate (normal rotation)

such that a rotational speed thereof is increased with a predetermined acceleration (ex. initial velocity: 60 milliliter/min; acceleration: 3 to 6 milliliter/min/sec) stepwise or continuously.

According to this, blood collection is suspended, and blood plasma in the blood plasma bag 21 is introduced to the blood storage space 55 via the tube 20 and the first line 2 to collect blood plasma which flows out of the outflow port 44 of the centrifugal separator 4 with the blood plasma bag 21 via the tubes 14 and 18. In short, blood plasma in the blood plasma bag 21 is circulated to the blood storage space 55.

<Process [6]>

When a circulation speed of blood plasma to the blood storage space 55 is reached at a maximum speed, namely, a rotational speed of the pump 9 reaches at a maximum speed (ex. about 130 to 250 milliliter/min), the controller 200 controls the valve 84 to close, the valve 83 to open, a rotational speed of the pump 9 to set, for example, about 20 to 100 milliliter/min and the pump 107 to operate.

Thus, blood of a donor is introduced again to the blood storage space 55 of the centrifugal separator 4 via the third line 10 and the first line 2 to collect the overflowed blood plasma with the blood plasma bag 21 via the tubes 14 and 18.

<Process [7]>

When a predetermined amount of blood plasma is collected with the blood plasma bag 21, the controller 200 controls the valves 83 and 85 to close, the valves 84 and 86 to open, the pump 107 to stop and the pump 9 to operate (normal rotation) such that a rotational speed thereof is increased with a predetermined acceleration (ex. initial velocity: about 40 to 150 milliliter/min; acceleration: about 3 to 20 milliliter/min/sec).

According to this, blood collection is suspended, and blood plasma in the blood plasma bag 21 is introduced to the blood storage space 55 via the tube 20 and the first line 2 while accelerating with the predetermined acceleration to collect blood plasma which flows out of the outflow port 44 of the centrifugal separator 4 with the blood plasma bag 21 via the tubes 14 and 18.

At this time, when blood plasma is circulated to the blood storage space 55 while accelerating with the predetermined acceleration, an interface between the buffy coat layer and the red blood cell layer is also shifted gradually to a side of the rotation central axis 900 because diffusion of the red blood cell layer occurs (a thickness of the red blood cell layer increases), and blood platelets are moved to the outflow port 44 of the centrifugal separator 4 (rotor 50) because the blood platelets in the red blood cell layer and the buffy coat layer float (fly up) resisting against centrifugal force.

<Process [8]>

When a circulation speed of blood plasma to the blood storage space 55 is reached at a maximum speed, namely, a rotational speed of the pump 9 reaches at a maximum speed, the controller 200 controls the pump 9 to maintain (retain) its rotational speed. The circulating speed of blood plasma to the blood storage space 55 is preferably set to about 120 to 300 milliliter/min, and set, for example, to 200 milliliter/min.

<Process [9]>

Parallel with Process [7] and Process [8], in a case that an output voltage (PC density voltage) of the optical sensor 62 became lower than a predetermined value (ex. about 2.5 to 3.5V), namely, density of blood platelets in blood plasma which flows in the tube 14 (second line 3) reached at a predetermined value or more when blood platelets flow out of the outflow port 44 of the centrifugal separator 4 (rotor 50), the controller 200 controls so as the valve 86 to close and the valve 85 to open.

Thus, platelet concentrate (PC) is introduced to and collected (stored) by the blood platelet bag 17. Incidentally, density of blood platelets continues to ascend after starting collection of the PC, and turns to descending after once reached at the highest density.

<Process [10]>

When density of blood platelets detected by the optical sensor 62 becomes a predetermined value or less, the controller 200 regards that collection of blood platelets to the blood platelet bag 17 is finished, and controls the pump 9 to stop in order to stop supplying blood plasma to the rotor 50, further, controls the rotation drive apparatus 7 to stop. According to this, collection of blood platelets is finished.

<Process [11]>

Then, the controller 200 controls the valves 83, 85 to open and other valves to close, and the pump 9 to rotate reversely. According to this, red blood cells, white blood cells and blood plasma remain behind the centrifugal separator 4 are returned to a donor via the inflow tube 47, the inflow port 43 and the tubes 13, 107.

At this time, such a structure may be employed that, when the judgment circuit 204 judges (predicts) that a donor may cause adverse reaction during collection of blood or after standing up from the blood collection bed, the controller 200 controls the pump 9 so as to lower a speed of blood returning or to stop (cancel or suspend) blood returning operation. Further, after or on way of this Process, the controller 200 may control the valves 84, 86 to open, other valves to close, to operate the pump 9 to run (normal rotation) in order to introduce blood plasma in the blood plasma bag 21 to the rotor 50 via the tubes 20, 13, the inflow port 43 and the inflow tube 47, subsequently, may control the valves 83, 85 to open and other valves to close, to operate the pump 9 to run (reverse rotation) in order to return blood plasma in the rotor 50 which is moved from the blood plasma bag 21 to a donor via the inflow tube 47, the inflow port 43 and the tubes 13, 101.

<Process [12]>

The above Process [3] to Process [11] are repeated and a predetermined amount of blood platelets is collected by the blood platelet bag 17. Then, the tube 16 adjacent to the blood platelet bag 17 is sealed, for example, by fusion, this sealed portion is further cut off and separated. Thus, a blood platelet bag 17, in which pharmaceutical preparation for blood platelet is contained, is obtained.

As stated above, in the blood component collecting apparatus 1 in this embodiment, since blood components such as blood plasma and the like and blood are supplied from a lower part of the blood storage space 55 and the interface of the separated blood components is shifted slowly and gradually, blood platelets are collected from the red blood cell layer and the buffy coat layer reliably without breaking or disturbing the interface and a collection ratio of blood platelets and an extraction ratio of white blood cells in the collected blood platelets are improved.

<Process [13]>

Next, the blood collection needle 104 is removed from a blood vessel of a donor and treatment for blood stanching is carried out. Then, after a while, a donor stands up from the blood collection bed. A donor to whom blood component collection is carried out according to the above stated blood component collection operation is likely not to cause adverse reaction such as VVR, faintness or the like.

Incidentally, an example that a biological information acquisition unit is constituted by the ECG 300 was shown in this embodiment. However, the biological information acquisition unit may be constituted by a pulse meter or both of the ECG and the pulse meter, in stead of the ECG 300.

Here, such a pulse meter can acquire (detect) pulse as biological information, and for example, detects continuously finger plethysmogram which occurs with heartbeat of a heart. At this time, a twice differentiated pulse wave (acceleration pulse wave) can be used preferably in order to detect an interval of pulses accurately. The HF values and the HF/LF ratio values can be calculated based upon an interval between adjacent pulses in the same manner as the above according to the same processing as the above.

For such a pulse meter, a sphygmomanometer and the like utilizing, for example, a finger plethysmography, an oscillometric method, a pressure pulse wave method or a method to which these are applied can be used. It is preferable for such a pulse meter, such as a wrist band type, a finger clip type, an ear clip type, a contact type or the like, that can detect pulse while a donor is putting on his/her closes. Such a pulse meter enables easy and accurate measuring of donor's pulse wave. Further, a sensor for the pulse meter may be disposable or reusable. Furthermore, the biological information acquisition unit may be constituted by an apparatus which monitors a width of a blood vessel continuously by image analysis in order to calculate the indicator for sympathetic activity and the indicator for parasympathetic activity.

In the foregoing, the blood processing apparatus which equips an autonomic nervous activity monitor according to the present invention was explained based on the illustrated embodiment. However, the present invention is not limited to the same. The structure of each of parts (units) may be replaced by an optional structure capable of exhibiting the same function. Further, if necessary, an optional structure may be added or omitted to/from the structure. For example, a blood processing apparatus according to the present invention is not limited only to a blood component collecting apparatus, but is applicable, for example, to a dialysis apparatus, a blood plasma exchange apparatus or the like. Moreover, the information processing circuit 202, the detection circuit 203 and the judgment circuit 204 may be constituted by software which operates the microcomputer in place of hardware.

Further, in the above embodiment, an example that an autonomic nervous activity monitor according to the present invention is applied to the blood processing apparatus was shown. However, the present invention is not restricted to a blood processing apparatus. The autonomic nervous activity monitor according to the present invention can be applied to a blood collecting apparatus that carries out blood collection operation to a body (a donor).

A technique, for example, disclosed in JPB5-54994 can be used for such a blood collecting apparatus. The blood collecting apparatus has a vacuum blood collection chamber of which pressure is reduced by a vacuum pump. In the blood collecting apparatus, a blood bag is set at the vacuum blood collection chamber, and the vacuum pump is controlled by a controller to reduce pressure inside the vacuum blood collection chamber, so that blood collection to the blood bag is carried out. In a blood collecting apparatus to which the present invention is applied, a blood collection unit is constituted by the vacuum blood collection chamber and the vacuum pump. Further, such a structure is employed that, when the judgment circuit 204 judges (predicts) that abnormal reaction may occur to a body (a donor), the controller 200 controls operation of the blood collection unit so as a blood collection speed to decrease or blood collection operation to stop (cancel or suspend).

Incidentally, it goes without saying that an autonomic nervous activity monitor according to the present invention can be used separately without combining with various blood collecting apparatuses. For example, in a case that a blood collecting apparatus which is independent from the autonomic nervous activity monitor is used for collecting blood from an examinee (normal subject or patient) and the autonomic nervous activity monitor is set to the examinee, when abnormal reaction may occur to the examinee after his/her standing up is judged (predicted) by the judgment circuit 204 and the judgment (prediction) is informed by the display unit 500, the autonomic nervous activity monitor can be used in a manner that a doctor or the like stops blood collection according to the blood collecting apparatus manually. Even in such a case, the autonomic nervous activity monitor is expected to demonstrate the effect that abnormal reaction that a donor may cause can be prevented from occurring in advance.

Further, an autonomic nervous activity monitor according to the present invention can be used not only for preventing abnormal reaction (adverse reaction) due to blood collection operation or blood drawing operation, but for predicting and preventing abnormal reaction which depends on autonomic nervous activity and which may occur due to various medical practices, or, occurrence of dizziness, dizziness at standing up or faintness which depends on various illnesses or activity of daily life (ex. eating a meal, bathing, standing up, running up stairs and the like).

What is claimed is:

1. An autonomic nervous activity monitoring method for predicting whether abnormal reaction may occur to a body, comprising the steps of:

measuring heartbeat or pulse of a body to acquire a pattern of the heartbeat or pulse as biological information;

calculating a value [$msec^2$] of a high frequency component (a HF value) defined as an indicator for parasympathetic activity and a value of a ratio of a low frequency component (LF) to the high frequency component (a LF/HF ratio value) defined as an indicator for sympathetic activity on a time-series base by carrying out frequency analysis to the acquired pattern of the heartbeat or pulse; and predicting whether abnormal reaction may occur to the body from a predetermined relationship between the HF value and the LF/HF ratio value, based upon the calculated HF values and the calculated LF/HF ratio values;

wherein, when alpha is defined as a predetermined coefficient, the predicting step predicts that abnormal reaction may occur to the body when the calculated HF value exceeds a predetermined reference value, and, when a sum of a period of {(the calculated HF value)>(the coefficient alpha)×(the calculated LF/HF ratio value)} becomes not less than 10% of a calculation period in the calculating step.

2. An autonomic nervous activity monitoring method according to claim 1, wherein the predetermined reference value ranges from 100 to 1000 [$msec^2$], the coefficient alpha ranges from 10 to 100 and the calculation period ranges from 2 to 10 [min].

3. An autonomic nervous activity monitoring method according to claim 1, wherein, when beta is defined as a predetermined coefficient, the predicting step predicts that abnormal reaction may occur to the body when a sum of a period of {(the calculated HF value)>(the coefficient beta)×(the calculated LF/HF ratio value)} becomes not less than 10% of a calculation period in the calculating step.

4. An autonomic nervous activity monitoring method according to claim 3, wherein the coefficient beta ranges from 25 to 500 and the calculation period ranges from 2 to 10 [min].

5. An autonomic nervous activity monitoring method according to claim 1, wherein, when alpha is defined as a predetermined coefficient and beta is defined as a predetermined coefficient which is larger than the coefficient alpha, the prediction unit predicts that abnormal reaction may occur to the body when the HF value calculated by the calculation unit exceeds a predetermined reference value and when a sum of a period of {(the HF value calculated by the calculation unit)>(the coefficient alpha)×(the LF/HF ratio value calculated by the calculation unit)} becomes not less than 10% of a calculation period carried out by the calculation unit, or, when a sum of a period of {(the HF value calculated by the calculation unit)>(the coefficient beta)×(the LF/HF ratio value calculated by the calculation unit)} becomes not less than 10% of the calculation period carried out by the calculation unit.

6. An autonomic nervous activity monitoring method according to claim 5, wherein the predetermined reference value ranges from 100 to 1000 [$msec^2$], the coefficient alpha ranges from 10 to 100, the coefficient beta ranges from 25 to 500 and the calculation period ranges from 2 to 10 [min].

* * * * *